US008424716B2

(12) United States Patent
Hegan et al.

(10) Patent No.: US 8,424,716 B2

(45) Date of Patent: Apr. 23, 2013

(54) WRISTBAND APPLICATOR

(75) Inventors: Bruce Ian Hegan, Buttaba (AU); Leigh H. Turner, North Adelaide (AU)

(73) Assignee: RFID n Print Pty Ltd., Morriset (AU)

( * ) Notice: Subject to any disclaimer, the term of this patent is extended or adjusted under 35 U.S.C. 154(b) by 121 days.

(21) Appl. No.: 12/681,469

(22) PCT Filed: Sep. 18, 2008

(86) PCT No.: PCT/AU2008/001385

§ 371 (c)(1), (2), (4) Date: Jun. 2, 2010

(87) PCT Pub. No.: WO2009/043084

PCT Pub. Date: Apr. 9, 2009

(65) Prior Publication Data

US 2010/0327002 A1 Dec. 30, 2010

(30) Foreign Application Priority Data

Oct. 2, 2007 (AU) ................................ 2007905382

(51) Int. Cl.

| | |
|---|---|
| ***B65D 83/08*** | (2006.01) |
| ***B65D 83/00*** | (2006.01) |
| ***A61B 5/117*** | (2006.01) |
| ***B65C 3/00*** | (2006.01) |
| ***G06K 19/06*** | (2006.01) |
| ***G06K 19/067*** | (2006.01) |
| ***G07F 11/00*** | (2006.01) |

(52) U.S. Cl.
USPC .................... 221/13; 221/9; 221/30; 221/282

(58) Field of Classification Search .................. 700/231, 700/232, 235; 221/9-10, 13, 30, 282; 40/633
See application file for complete search history.

(56) References Cited

U.S. PATENT DOCUMENTS 5,878,909 A * 3/1999 Rogow ............................ 221/45
6,782,648 B1 * 8/2004 Mosher, Jr. ...................... 40/633

(Continued)

FOREIGN PATENT DOCUMENTS

WO WO 94/11190 A1 5/1994

OTHER PUBLICATIONS

International Search Report of PCT/AU2008/001385 dated Nov. 4, 2008.

*Primary Examiner* — Michael K Collins
(74) *Attorney, Agent, or Firm* — Venable LLP; Robert Kinberg

(57) ABSTRACT

The present invention concerns apparatus for efficiently dispensing and applying a wristband identification bracelet that is meant for attachment around an extremity of an animal or person. The apparatus is provided with a supply of identity bands that are adapted to become a bracelet by having a first portion of the band affixed to a second portion to form a continuous loop around the extremity. The extremity is positioned within a receptacle in the apparatus, permitting the identification band to be wrapped closely around the extremity by the band fixing mechanism of the apparatus. The identification band is fixed to itself to form a bracelet, so as to prevent its removal from the extremity without damaging the integrity of the bracelet. The identification bracelet comprises an integral RFID inlay component, and particularly an RFID component whereby all of the RFID circuit is realised in low cost fully printed silicon ink TFT semiconductor form as opposed to a conventional integrated circuit (IC) chip used in prior art RFID inlays.

13 Claims, 12 Drawing Sheets

U.S. PATENT DOCUMENTS

| | | | | |
|---|---|---|---|---|
| 7,317,965 | B2 * | 1/2008 | Koyama | 700/233 |
| 7,635,067 | B1 * | 12/2009 | Flynn | 221/45 |
| 2005/0108912 | A1 | 5/2005 | Bekker | |
| 2007/0029377 | A1 | 2/2007 | Hinckley | |

* cited by examiner

Fig 6d(ii)

WRISTBAND APPLICATOR

CROSS-REFERENCE TO RELATED APPLICATIONS

This application is a National Stage Application of PCT/AU2008/001385, filed Sep. 18, 2008, which designates the United States and claims the priority of Australia Patent Application No. 2007905382, filed Oct. 2, 2007.

TECHNICAL FIELD

The present invention relates to apparatus and a method for applying identity bands to an extremity of a person or animal, such as for applying a wristband to the arm of a person. Preferably the invention involves an integrated apparatus for dispensing and applying such a wristband. In particular, it also relates to a wristband containing an information bearing serialised ID or Radio Frequency Identification (RFID) transponder, which can be applied using such apparatus.

BACKGROUND ART

The present invention relates to apparatus and a method for applying an identity band or bracelet to the wrist of a person for example. Traditionally, a wristband carrying some identification information, such as a colour or logo, barcode, serial number, or RFID inlay, for example, is provided to a person, who then generally affixes it around their own wrist. Such a wristband operates to identify the person in a venue, such as in an amusement park, at a ski-lift and so on. It permits the person wearing the band to enter the venue or access a ride, and so on. These types of wristbands normally function as a form of non-removable identification, to be retained on a wrist, for instance, so as mark a person authorised to enter a venue such as a concert, sports match, theme park, or the like. The wristband is normally constructed to be difficult or impossible to remove, without damaging or otherwise making the act of removal or tampering noticeable. This tamper evident construction improves its security function, to prevent the identification band being swapped or given to another person once fixed around the first person's wrist.

Commonly, such a band is provided at the entrance to the venue, or when purchasing a ticket, in the form of a preprinted strip of tough paper or plastic type of material, which is of a size suitable for being looped around a wrist, and with an adhesive patch at one end, which can be adhered to the surface of the other end of the band, to form a firm-fitting bracelet around the wrist. The fit preferably should not be so loose as to slip over the hand and be removed.

Normally, the adhesive patch has a removable siliconised liner cover that must be removed to expose the adhesive area prior to it being fixed to the other end of the band. This cover material must then be disposed of, which creates waste, and the removable cover can create a hazard if not disposed of correctly.

Also the manufacture is more difficult, and expensive, of wristband stock that contains an adhesive area, and a cover to protect the adhesive area until it needs to be used.

The area containing the adhesive, and possibly the area the adhesive is affixed to, is often deliberately weakened, such as by distressing the area with a number of slits in the material, so that any attempt to unfasten the band once affixed, further damages or destroys that portion of the material. This usually renders the band's tampering noticeable, and will usually prevent the band from being re-joined. Normally, the wristband has an adhesive that cannot easily be re-joined after its initial mating, and if the adhesive is also positioned over a distressed or weakened area, this area will be damaged if an attempt is made to open the band once it has initially been fixed together. Tampering with the band, once applied, should therefore be noticeable, and would usually destroy the integrity and utility of the wristband.

RFID inlays are commonly used to impart an RFID function to a wristband. Such RFID inlays of conventional construction utilise a small single-crystal silicon CMOS (Complementary Metal-Oxide-Semiconductor) integrated circuit (IC) die that is flip-chip bonded to the antenna element and flexible supporting substrate. However, this traditional method of RFID circuit realisation is often too expensive for incorporation into many highly cost sensitive mass consumer type applications for RFID technology, such as disposable single-use and short life cycle wristbands used for event ticketing and entertainment venue access control or for short-lived stored value e.g. monetary or privilege credits. The present invention also involves a preferred method of wristband RFID tag construction based on printable silicon ink semiconductor materials. This novel method of electronic circuit realization has been previously disclosed by Kovio Inc. of Milpitas, Calif., USA. This key semiconductor enabling technology is optimally suited to manufacturing very low cost RFID circuits for use in the feedstock for the wristband applicator of the present invention.

In addition, it is normally important to maximise the security of such a band to ensure that the wristband is fastened closely around a person's wrist, so as to prevent it being removed by being slipped off the wrist over the hand. A person trying to subvert the security of the wristband may try to fasten the band loosely around their own wrist, to allow it to be slipped off, and passed on to another person. The issuing authority will want to ensure a tight fit around a wrist, to prevent the band being slipped off, and passed to another person. But this snugness of fit is hard to arrange, when the user must apply the band to their own wrist. To ensure a tight enough fit, with the conventional system, often security staff will need to be employed to visually inspect the fit of the band, at the initial entry point. Any loosely fitted bands will then need to be reallocated which adds to the cost and complexity of the entry process.

In amusement parks, for instance, there may be a problem if one entry band is purchased and passed around a number of persons who share the band to take part in a number of different rides, instead of each person purchasing their own wristband. As well as reducing income to the amusement park owner in this instance, there may be safety and public liability issues, if a band is coded to admit the wearer only to rides appropriate to their age and height. If bands can be swapped to other people, then these safety restrictions can be avoided or subverted.

It is therefore often difficult for the issuer of the wristband to make sure that the band is attached closely and tightly enough to the wrist of a person so as to prevent it being removed without having to be pulled apart. In some instances, personnel have to be supplied by the event organisers to assist patrons with applying the wristbands. It is necessary to take into account the possibility of a person attempting to subvert the purpose of the band by fastening it too loosely around their own wrist, in order to allow it to be easily removed by slipping it from their wrist, over their hand. Or else, a person may accidentally attach the wristband too loosely, which can easily allow it to fall off and be lost. Or there may be other innocent explanations to cause this problem, such as applying the band over gloves, wristwatches or other clothing or jewellery, which can allow the band to be able to be removed easily from a wrist, without destroying its physical integrity.

Preferably, such an automated wristband applicator apparatus may be a desktop model, or it may be attached to a kiosk, so as to enable the redemption of an online purchase for example. It would also be useful to provide a wristband that can avoid the use of a liner cover over the adhesive portion, which would otherwise need to be disposed of. Such adhesive closures have in the past been recognised as a major problem in regard to waste disposal and occupational safety. For instance, this may occur where the removable cover strips are discarded indiscriminately to cause serious safety issues if patrons should walk and slip on the exposed slippery silicone surface of the discarded cover strips. By applying the requisite adhesive tab as an introduced component to the wristband at the time of closure via the wristband applicator several desirable safety and cost efficiencies can be obtained.

Another common complaint from event organisers is the time it takes to separate the wristbands that are manufactured in sheets and then sell the individual wristbands to a patron, given the propensity for the majority of patrons to arrive at a venue just before the scheduled starting time for an event, which creates a large crowd. This congestion is further compounded should the patrons then have difficulties in applying the wristband to their wrists. It would therefore be useful if the wristband could be provided, and preferably also applied, by means of a standalone dispensing machine, or kiosk. This would allow patrons to redeem any prior ticket purchase, over the internet for instance, and then to have a wristband applied properly to their wrists, without the need for much supervision. This would help event organisers, by reducing or eliminating queues prior to the commencement of the event. There would also be a cost saving, by avoiding the need for additional supervisory personnel who would otherwise be required to assist patrons in properly applying the wristbands.

It would therefore be an advantage if a wristband can be provided that would overcome at least some of the disadvantages of previously known wristbands, or would provide a useful alternative to these. In particular, it would be useful to provide an automated system of applying a wristband to the wrist or other extremity of a person, for instance, to consistently fasten it closely to a wrist. This system may ideally involve an integrated apparatus for dispensing and applying the wristband, and also to a type of wristband that may be applied using such apparatus.

DISCLOSURE OF THE INVENTION

The present invention concerns apparatus for dispensing and applying an identification bracelet that is meant for attachment around an extremity of an animal or person. The apparatus is provided with a supply of identity bands that are adapted to become a bracelet by having a first portion of the band affixed to a second portion to form a continuous loop around the extremity. The extremity is positioned within a receptacle in the apparatus, permitting the identification band to be wrapped closely around the extremity by the band fixing mechanism of the apparatus. The identification band is fixed to itself to form a bracelet, so as to prevent its removal from the extremity without damaging the integrity of the bracelet.

Preferably, all the dispensing and identity bracelet application functions are integrated within the apparatus.

Preferably, the most common extremity that the bracelet will be applied to is the wrist of a person.

Preferably, the band is provided in the form of a continuous strip feedstock, which is cut to a suitable length by the cutting mechanism of the apparatus. Alternatively, the band is provided in the form of a multiplicity of discontinuous strips, each of which is individually applied to an extremity by the apparatus.

Preferably, the band has identification information, such as a barcode, or OCR data applied to its outer surface by printing, or an RFID tag laminated within the band. This is attached by the information application mechanism of the apparatus, for example, a printer or RFID inlay dispenser.

Preferably, the apparatus has a seal application mechanism that applies a separate adhesive seal to the surface of the band. This overlaps the first and second portions of the band and is used to fix the two portions of the band together to form a bracelet.

Preferably, the apparatus has an auto-tensioning mechanism, to tauten the band close to the surface of the extremity, but to still allow for a full range of circumference sizes of the extremity to be used in the apparatus.

Preferably, the apparatus has a self-adaptive length dispensing mechanism to cater for a full range of circumference sizes of the extremity.

Preferably, the apparatus has a cutting mechanism to cut the length of the band to a suitable length.

Preferably, the apparatus has a control mechanism to govern the operation of the apparatus.

Preferably, the apparatus has an information reading and analysis mechanism that can read any form of identification on the band, and can confirm that it is correct, or alternatively, can provide a warning if the identification cannot be read.

Preferably, the apparatus has positioning means to ensure that the extremity is optimally positioned within the apparatus so that the band is applied around the correct area of the extremity.

Preferably, the apparatus has a hand grip, arranged so that by holding the grip, the extremity of the person is properly positioned in relation to the apparatus in order to receive the band.

Preferably the apparatus is installed in a standalone kiosk, where the kiosk also has means to accept payment from a person, prior to issuance and application of the wristband.

Preferably, the apparatus has a means to identify the person, and to confirm their right to enter a venue, before issuing and applying the wristband to an extremity of the person.

The present invention also concerns the identity band for use in the aforementioned apparatus.

Preferably, the apparatus is provided with a supply of these identity bands. Each is adapted to become a bracelet by having the first portion of the band affixed to the second portion in order to form a continuous loop around the extremity.

Preferably, the bracelet is affixed to itself by means of a separate adhesive seal that is applied to the surface of the band. This overlaps the first and second portions of the band and is used to fix the two portions of the band together to form a bracelet.

Preferably, the seal comprises a first inner layer and a second outer layer. The inner layer is a thin adhesive layer with a low physical integrity and the outer layer is of a material that is sufficiently strong to retain the bracelet together. The inner layer adheres the outer layer to the band. The adhesion of the inner side of the first inner layer that attaches to the band surface is stronger than the adhesion of the outer side of the first inner layer that attaches to the second layer. An attempt to remove the second layer thus leaves the inner layer adhering to the band.

Preferably, the inner layer of the seal has information, mainly text, such as the word "void", or similar word or words, displayed on its outer surface. This information thus becomes visible when the outer layer is removed.

Preferably, the identity bracelet further includes an RFID functional inlay component comprising electronic circuitry created entirely by means of a semiconductor printing process. The RFID functional inlay component preferably comprises two elements; a silicon CMOS integrated circuit (IC) combined on a common substrate with an antenna. The CMOS integrated circuit is implemented using nanoparticle formulated "silicon ink" materials to create complementary P and N channel thin-film-transistor (TFT) semiconductor devices, and the antenna element is printed with conductive metal particle ink. Preferably, the RFID functional inlay component operates at a frequency of about 13.56 MHz.

Preferably, the antenna is formed by high speed ink-jet deposition directly onto a substrate carrier comprising a polymer plastic material band. The identity bracelet is preferably substantially of a laminated polymer plastic material band, which is attachable around an extremity of an animal, including a person, by a bracelet applicator device.

According to one preferred embodiment of the present invention, the RFID functional inlay component and the antenna are sandwich laminated into the polymer plastic material band. In another preferred embodiment, the RFID functional inlay component and the antenna are hermetically sealed into the polymer plastic material band. In both embodiments, it is preferred that the RFID functional inlay component has a polymer backing layer.

The identity bracelet is preferably attachable around an extremity of an animal, including a person, said bracelet being attachable by means of an apparatus, said apparatus including a reel containing a large number of the singularly printed CMOS silicon ink based RFID inlay circuits, providing a bulk feedstock for automated dispensing of RFID enabled bracelets.

In another embodiment, the identity bracelet is preferably attachable around an extremity of an animal, including a person, said bracelet being attachable by means of an apparatus, said apparatus including a reel containing a large number of singular CMOS IC-chip based RFID inlay circuits, providing a bulk feedstock for automated dispensing of RFID enabled bracelets.

Preferably, the RFID functional inlay component and the antenna are inserted into the bracelet by the apparatus during the continuous wristband lamination process. In another embodiment, the RFID functional inlay component and the antenna are integrally formed with the bracelet during the continuous lamination process.

BRIEF DESCRIPTION OF THE DRAWINGS

The invention will now be described, by way of example only, with reference to the accompanying drawings, where.

BEST MODES FOR CARRYING OUT THE INVENTION

Figure 1:
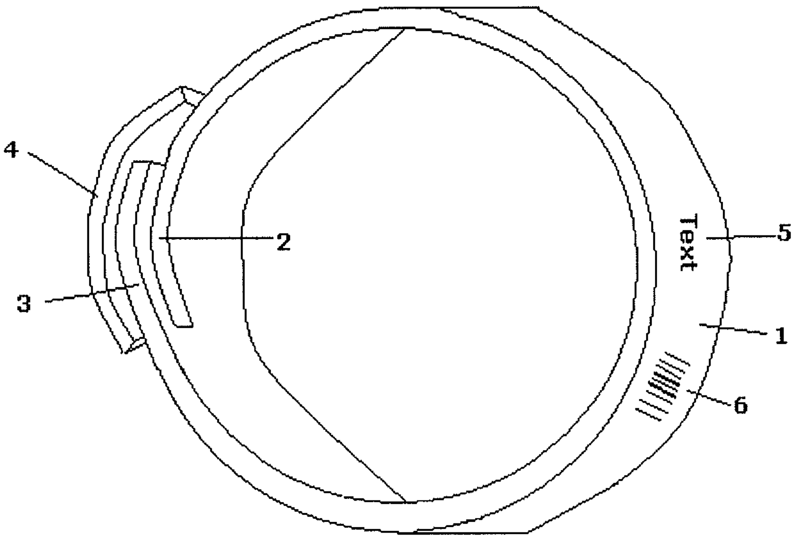
FIG. 1 shows a wristband according the invention fastened together (but without displaying a wrist around which it normally would be positioned)

In the drawings, FIG. 1 shows a wristband for use in the present invention. The wristband is shown in the form as it would be fixed around a wrist of a person wearing the wristband, but the wrist is not shown.

In FIG. 1, the bracelet 1 is composed of a band having a length suitable for going around a wrist of a person, and having two ends 2, 3 which overlap. These ends may be held together by a seal 4. The identification bracelet 1 contains information on its outer surface, such as alpha-numeric character text 5 or a barcode 6. These two ends 2, 3 may overlap, by one end being juxtaposed on top of the other end, or else the two ends may be juxtaposed side by side. An end may be overlapped with the same side of the band, i.e., the outer-side of the band over or alongside the outer-side of the other end of the band, or the inner sides of the band, i.e. the inner side of one end affixed to the inner side of the other end. The band is preferably laid flat around the extremity, but may be twisted, such as a by a half turn, or a full turn, in some situations where this is desirable.

If weakened or distressed areas are utilised with the wristband, then these areas may be preformed in the band material. Alternatively, the band material may be distressed by the machinery that is to apply the band around the wrist. If a separate seal is used to hold the band together, then this may also, or instead, be weakened or distressed. The distressed region, which is commonly a number of overlapping perforation slits or cuts, often in a star shape, may be applied to the seal material at the time of its application, or else preformed in the material. Often the distressed area will sit on a removable and undamaged backing layer, which is pealed away, before the ends of the band are joined together, with the adhesive sections overlapping mostly with the distressed area or areas.

Figure 2:
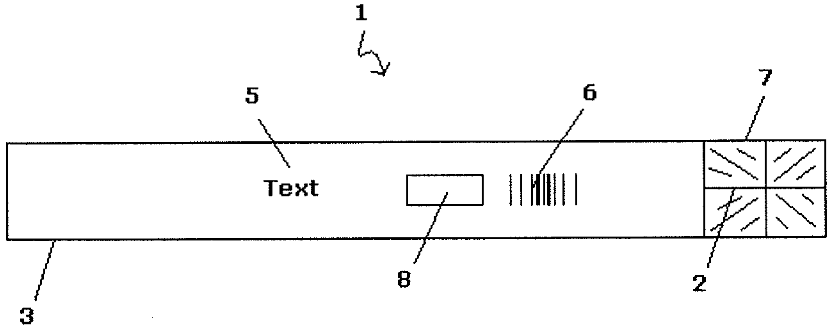
FIG. 2 shows one embodiment of a wristband before it is fastened together.
Figure 3:
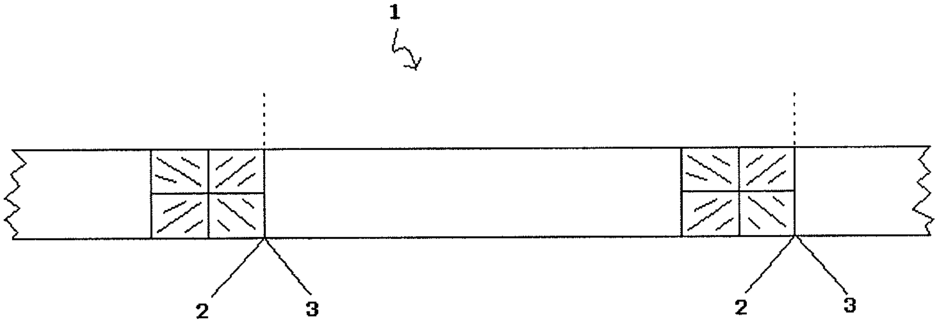
FIG. 3 shows an alternate view of the wristband of FIG. 2 as a continuous strip.

Another alternative to the band is shown in FIG. 2 and FIG. 3. In FIG. 2, there is a weakened and scored area 7 located at one end of the strip 2. This area may have a number of slits in this area, and, as one alternative, this area may be covered with contact adhesive, in the traditional manner. Textual material 5 that may be details of the venue with which the bracelet is to be associated, images and logos or third-party advertising material, and preferably some unique identification such as a barcode 6 on the outer surface of the band at the time of issuance of the band. Or there may be an RFID tag/inlay 8, printed or included on, or incorporated within the material of the band. This RFID tag/inlay subassembly component may be pre-printed or incorporated into (or attached to/laminated into) the band material beforehand, or at the time of the band's processing through the machine 1.

As one alternative, the traditional band as shown in FIG. 2, may be utilised with the present invention. Alternatively, and preferably in accordance with the present invention, the band may be formed into a bracelet using a separate seal 4 which overlaps with two sections of the band material, affixing them together, as shown in FIG. 1. If desired, both approaches may be utilised together.

One such separate seal may be used, or else two or more may be used on the one band. Two seals may be used, with one on each side of the band material. The seal may also be folded around the ends of the band material. The band material may be further folded onto itself, and the same, or another seal may be applied to further bind the material to itself, to form a closely held wristband.

In FIG. 3, another alternative of the invention is shown, where the identity bands 1 are provided in a continuous strip. There may be perforated sections separating an end 2 of one strip from the other end 3 of another strip. Such weakened areas 7 may be pre-formed in the original stock, or else cut into the strip within the attachment machinery. Otherwise, the strips may be cut apart when they are applied, taking the material from a long roll. This allows the strips to be cut to size by the apparatus for producing and dispensing the identification bracelets.

Preferably, the strips fit closely around the wrist. The most preferred arrangement is for the wristband to fit tightly enough so that it cannot be removed by allowing it to be slipped over the hand. However, in some situations, the strip may be permitted to hang loosely around the wrist, or other extremity of the wearer. As the wristband must be able to be applied on different sized wrists, from those of children to large adults, there is ideally a method of their application which easily allows for this. Such a self-adaptive length dispensing attribute is a key feature of the apparatus of the present invention.

As one approach, the strips that are formed into the bracelets may be of a standard length, in which case they are overlapped by differing lengths, so as to fit closely around different sized wrists. This approach works best for non-continuous bands, or with continuous strips that have pre-formed features on them, such as text or weakened areas. Otherwise, they may be cut to size, as they are applied to a person's wrist, which maximises the number of strips that fit on a continuous roll, and minimises wastage. It is also possible to combine both approaches, by having a standard size strip that is cut shorter upon being fitted around a wrist, or by having a standard sized section, optionally containing pre-printing, and a tail section that may be shortened upon application.

A variety of different arrangements for a wristband that can be applied by a machine to a person's wrist are shown in FIGS. 6*a* to 6*f*. Similar features in each of the alternative embodiments are identified by the same numbers.

In these FIGS, a wristband 1 is shown affixed to itself, and positioned around a wrist 9. In these examples, the band is joined to itself after having been arranged appropriately around the wrist by means of a seal 4, which is affixed to both ends of the band material to then hold it in place.

Figure 6A:
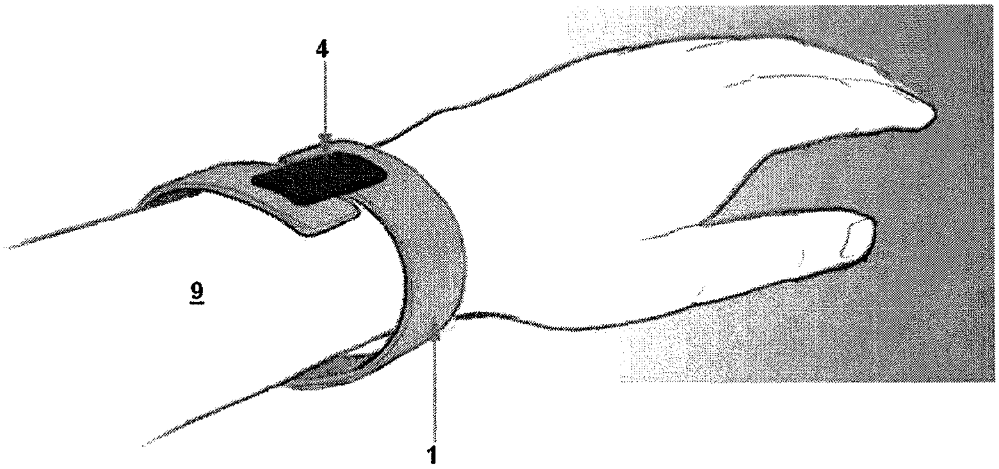
FIGS. 6*a*, 6*b*, 6*c*, 6*d*, 6*e* and 6*f* show a variety of different wristbands in accordance with the present invention, positioned around a wrist.
Figure 6B:
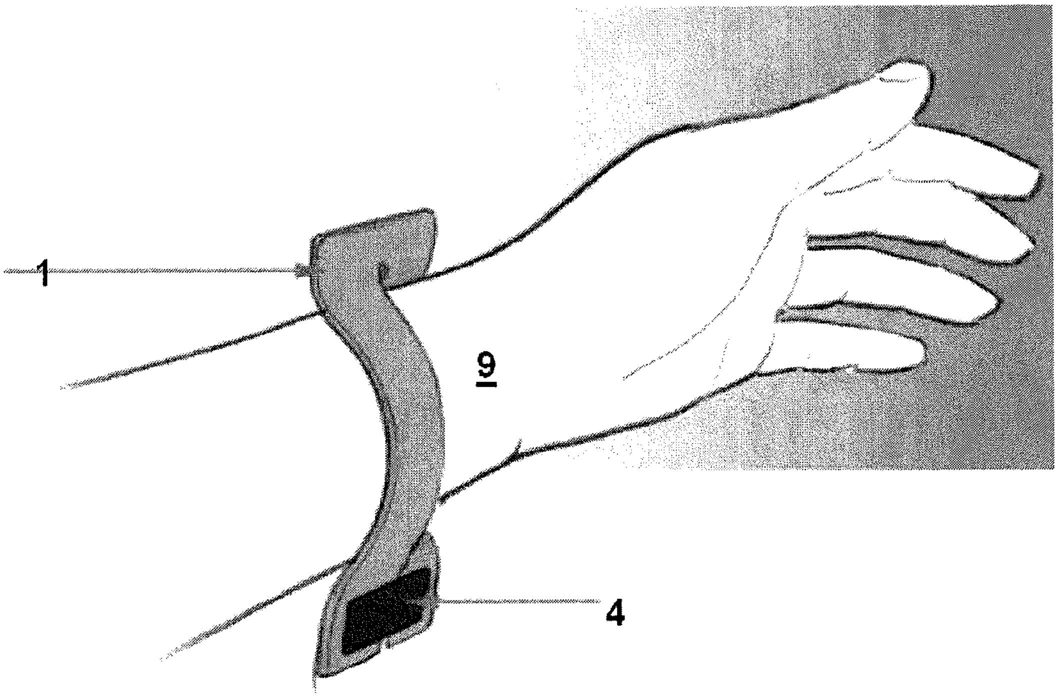

In FIG. 6*a*, the band 1 is wound around the wrist, and the two ends are positioned side by side, allowing the seal 4 to sit across both sections near to the two ends. FIG. 6*b*, shows another alternative, where the wristband material is wide, and has a lengthwise slit or cut created along a significant portion of its length. The wrist is positioned within this slit, with one side of the band appearing on each side of the wrist. A seal 4 is used to join the open ends of the band together.

Figure 6C:
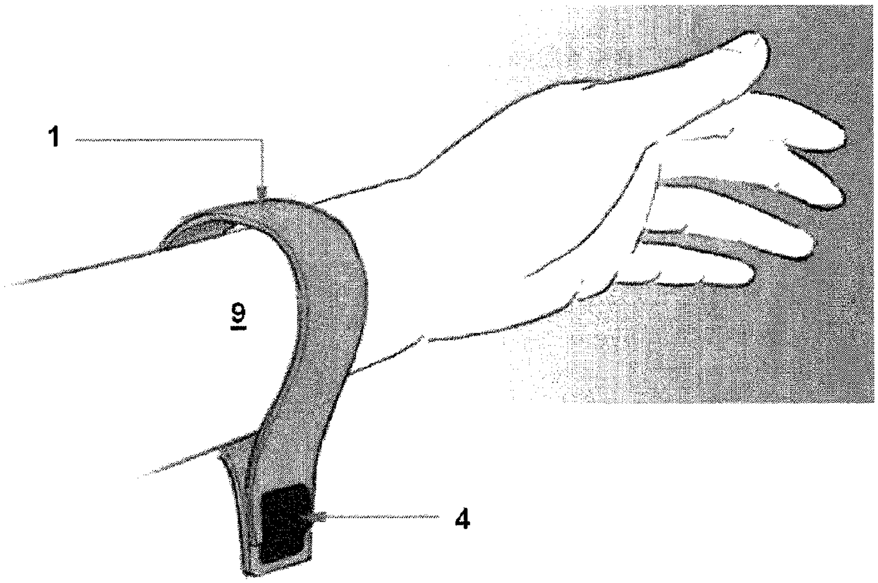
Figure 6D:
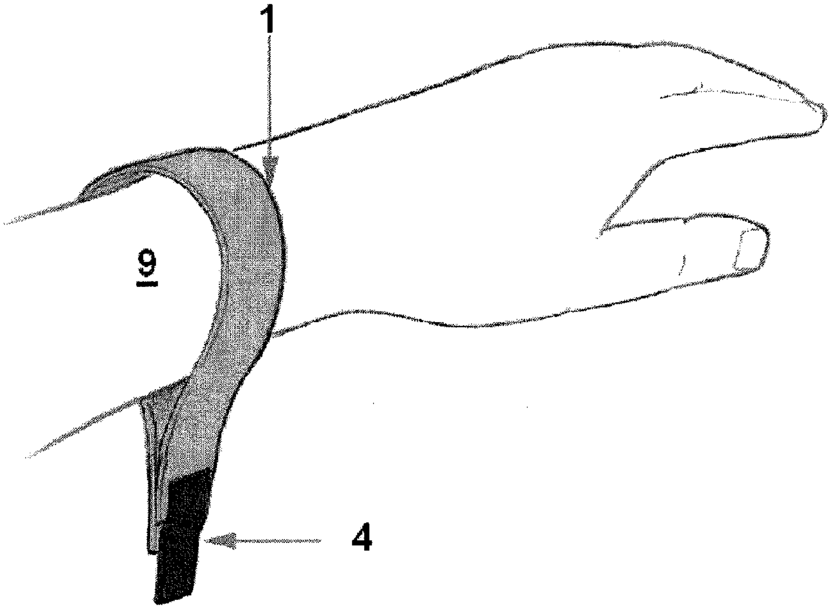
Figure 6E:
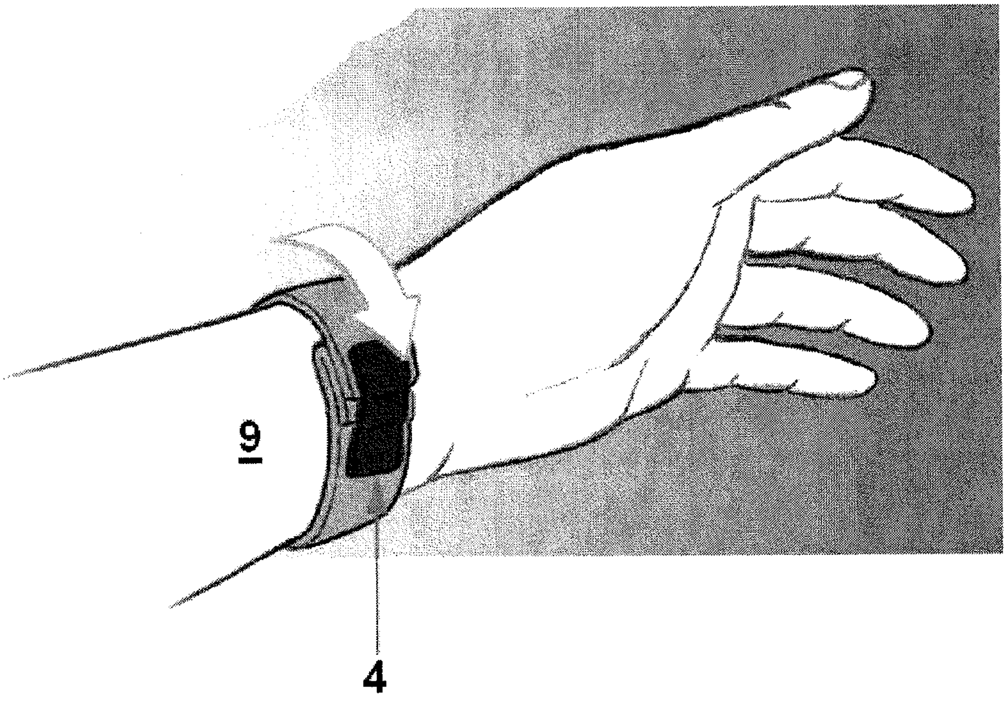
Figure 6E:
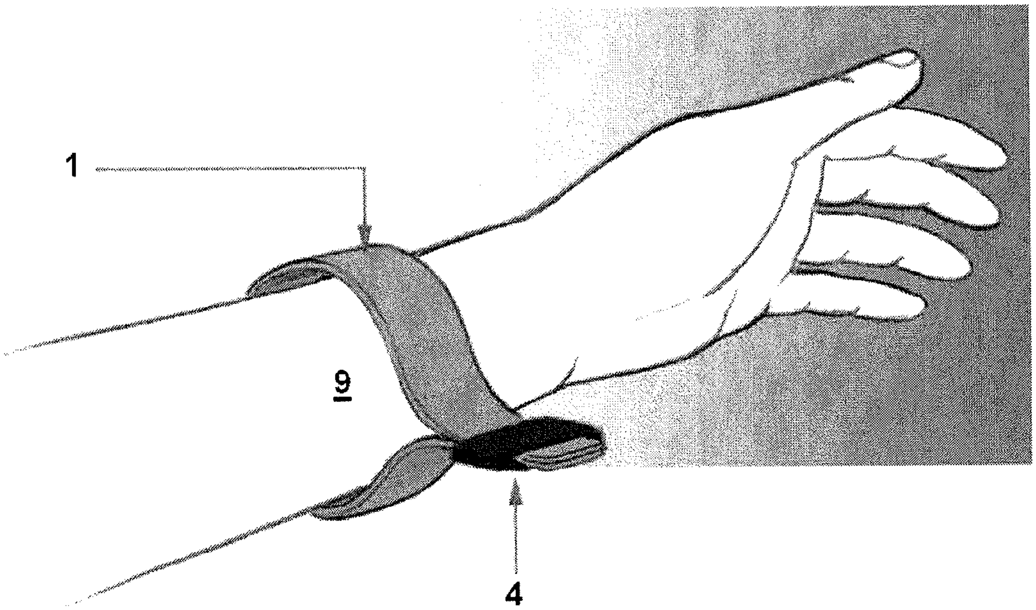
Figure 6F:
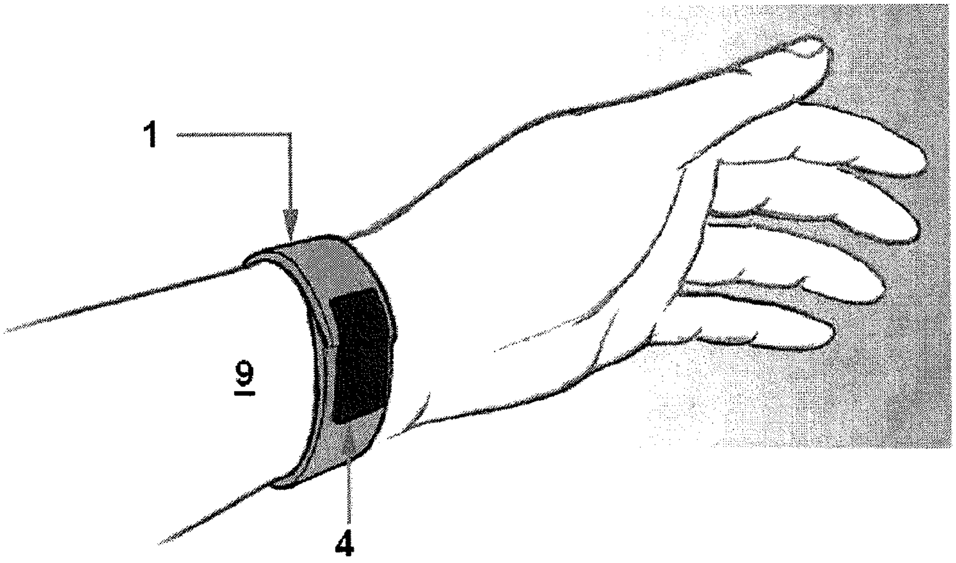

FIGS. 6*c* and 6*f* show the ends of the band 1 overlapping, and sealed together. In FIG. 6*c*, the inner sides of the band material are positioned against each other, and a seal 4 is applied across the edge of the shorter end, to adhere to the other end, in the style of a cufflink. In FIG. 6*f*, the more traditional arrangement is shown, (as in FIG. 1), where the inner side is positioned across the outer side of the other end, and the seal 4 overlaps both.

In FIG. 6*d*, another alternative is shown, where the band is joined as in FIG. 6*c*, but using a longer seal 4, which firstly, as in FIG. 6*d*(i), joins the shorter end to the longer portion with some excess portion of the seal then used to allow the joined ends to be folded back against the remainder of the band, and be adhered there, as shown in FIG. 6*d*(ii). FIG. 6*e* shows another approach, where the seal 4 is folded twice around the two ends of the band, and allowed to adhere to itself.

The seal 4 used in these examples, may itself contain unique identification, in addition to, or instead, of that appearing on the wristband. For example the seal 4 may have a barcode printed on it, or it may contain the RFID tag. Preferably, the seal is made tamper evident, such as by being weakened, or distressed, so that attempts to loosen the adhesion, once affixed, will be readily apparent, and damage the wristband.

The RFID functional component 8 of the wristband of the present invention is preferably produced by electronic circuitry created by means of an inexpensive semiconductor printing process. The CMOS circuitry is implemented using nanoparticle formulated "silicon ink" materials to create P and N channel thin-film-transistor (TFT) devices and an associated conductive antenna element formed by high speed ink jet deposition or patterned by other circuit creation means, such as photolithography, directly onto a thin and flexible substrate carrier. This process has an advantage over other conventional RFID enabled devices by providing relatively inexpensive, mass produced articles utilising RFID technology.

The highly secure and forge-proof "printed silicon" RFID functionality can also be augmented or complemented by traditional barcode or optical character recognition (OCR) data and identification information that is printed on the external surface of the wristband for reading by conventional optical barcode scanners and character recognition equipment.

The planar RFID circuit and its antenna may be sandwich laminated and hermetically sealed into the polymer plastic wristband material and can be either a separately inserted element or comprise a layer integral to the continuous wristband lamination. The RFID circuit, and particularly its antenna, operate at a nominal interrogation frequency of 13.56 MHz. However, it should be understood that any suitable radio operating frequency can be utilised.

Figure 4:
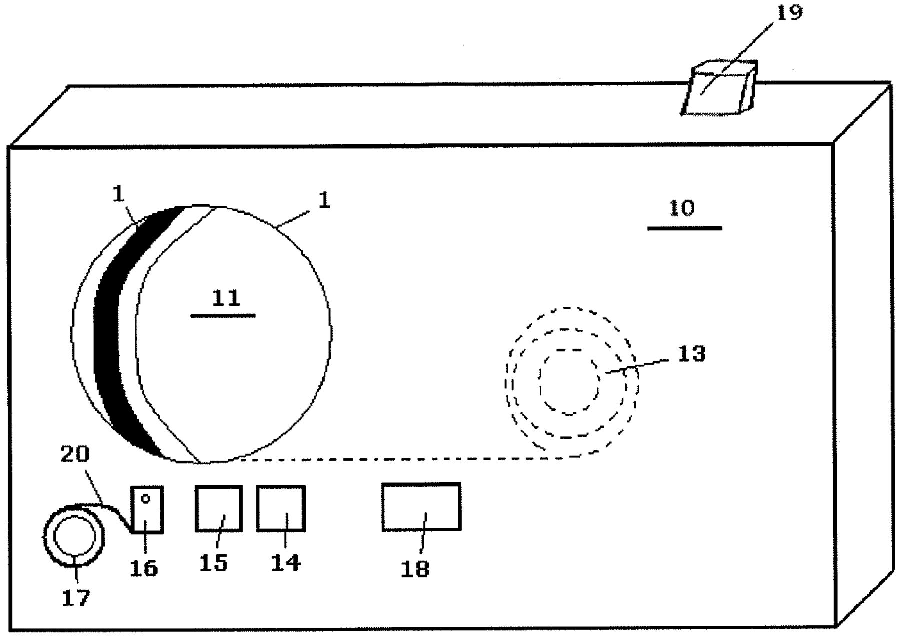
FIG. 4 shows one embodiment of a general schematic of an apparatus for applying the wristband around a wrist.

A general schematic of the apparatus for producing and dispensing an identification bracelet is shown in FIG. 4. This shows a generalised apparatus 10 having an aperture 11, into which the extremity of a person (or animal) may be introduced.

The aperture 11 may be of any suitable shape and size. It may be a hole, as shown in FIG. 4, into which a hand is thrust, so that the person's wrist is located at the optimum spot for having an identity band wrapped around the wrist of the person. Otherwise, the aperture 11 may be a slot, or a flat area of the top or side of the apparatus 10, which would then allow one or more engagement arms to dispose themselves around the wrist of the person to wrap the wristband around the person's wrist. In the generic example of an apparatus 10 for applying a wristband on person as shown in FIG. 4, there is a continuous strip 1, which is disposed around the aperture 11 of the dispensing apparatus 10.

The apparatus 10 may operate with identity bands that are provided to the machine in the form of a continuous strip 1, or else with a supply of bands that are in the form of individual strips. In the generic example of FIG. 4, there is a continuous roll of feedback strip material 13 to act as the supply of identity bands.

There is preferably also automatic tensioning means 14, which can tighten the strip 1 around a wrist, until the band is a close fit. There is also cutting means 15 which cuts the end of the strip at the appropriate place. This may be auto-tensioning, so as to cater for a full range of the circumference sizes of the wrist or other extremity.

The apparatus may have self-adaptive length dispensing means to cater for a full range of the circumference sizes of the wrist. This permits the machine to dispense the appropriate length of band material for the wrist (or other extremity) around which it is being wrapped. Alternatively, or in addition, the excess material may be doubled up over the other end of the band.

The apparatus 10 also includes a seal applicator device 16, which applies the seal 20 to the area where the two ends of the band now overlap. The seals 20 may be provided in the form of a continuous roll 17.

A printer 18 is also an integral part of the apparatus 10. The printer 18 may add unique identification to the bracelet on the side that will become the outer surface of the bracelet. This information may be a barcode or other variable data, for instance. The printer 18 may be a thermal laser printer or an inkjet printer. Alternatively, or in addition, a printer 18 may also print on the seal. All of the features included in the apparatus 10 are preferably integrated within the body of the apparatus, and cooperate together. This may also involve having an integrated control panel, to select and switch on/off the machine or its constituent components. An attractive, integrated casing is also a preferred feature of the apparatus, which may also assist with consumer acceptance of its use.

The apparatus 10 also preferably has control means 19, so as to govern its operation. This may be a button, which is pressed to start the process. There may be a separate button to release the wrist and allow the person to remove their arm from the apparatus. Otherwise, this entire application and release process may be effected automatically via appropriate sensors.

The apparatus 10 also includes a reel containing a large number of singular "printed silicon ink" or conventional IC chip based RFID circuits on a polymer backing layer. This bulk feedstock of either printed or conventional RFID circuits allows for the automated dispensing of RFID enabled wristbands from the apparatus 10.

The apparatus 10 may also have some information reading and analysis means, that can read any identification on the band, and confirm that it is correct, and which provides a warning if the identification cannot be read. For example, the apparatus 10 may have an integral RFID reader to read and write the RFID inlays. Additionally to or instead of the RFID reader there may be an integral barcode scanner to read optical barcodes. Therefore, if the band has a barcode or RFID tag on it, this is read, while the person's wrist is still in the machine, and if any error occurs in this analysis, the apparatus sounds a warning. For example, a person may shake the machine or move their wrist while the band is being applied, which may cause the data to print incorrectly. The apparatus 10 attempts to read and verify the barcode, before releasing the wrist, and if it cannot, a warning buzzer may sound. Similarly, it may read, program or verify any RFID tag once the band is applied around a wrist, and if the tag or encoded data should be faulty, sound a warning buzzer. The apparatus may also have an internal waste bin receptacle to capture the unwanted adhesive liners and any defective RFID inlays.

The apparatus 10 may also have some positioning means, to ensure the person's extremity, such as an arm/wrist region, is positioned in the best place, so that the band is applied around the wrist, or to the optimum place. With a human forearm, this may comprise a stop, which the person's fist rests against. Or else it may comprise an elbow stop, to achieve the same result of the band being attached around the person's wrist, or the narrowest section of the arm. As another alternative, there may be a grab-bar which the person may hold on to, to position their wrist at an appropriate position, with respect to the machinery.

In FIGS. 7*a* to 7*f* some examples of wristband application machines are illustrated. In FIGS. 8*a* to 8*f*, the path the wristband material takes in the corresponding applicator machine is indicated. The resulting orientation of the wristband on the person's wrist is shown in FIGS. 6*a* to 6*f*. In this way, the path of material of FIG. 8*a* corresponds to the apparatus FIG. 7*a*, which corresponds to the wristband of FIG. 6*a*, and so on with the rest of FIGS. 6*b* to 6*f*, 7*b* to 7*f* and 8*b* to 8*f*.

Figure 7A:
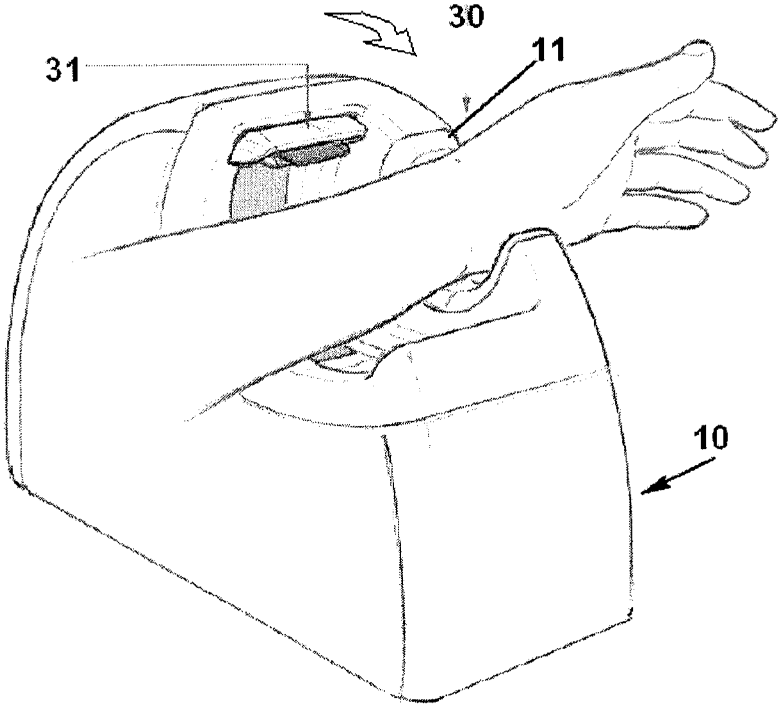
FIGS. 7*a*, 7*b*, 7*c*, 7*d*, 7*e*, and 7*f* show a variety of different embodiments of a machine for applying wristbands around a wrist, especially for applying the bands shown in the corresponding FIGS. 6*a* to 6*f*.

In FIG. 7*a*, an apparatus 10 is shown with a slot aperture 11 that engages with a person's arm. There is a rest moulding 30 for the person to rest their hand on, which is smaller than the general aperture. A radial arm 31 rotates over the arm, to feed the wristband across the wrist. The band material follows the path 32 shown in FIG. 8*a*, and the seals follow the path 33. The strip is cut, and a seal is applied across both ends, which are staggered, and positioned side by side, to create a wristband as shown in FIG. 6*a*.

Figure 7B:
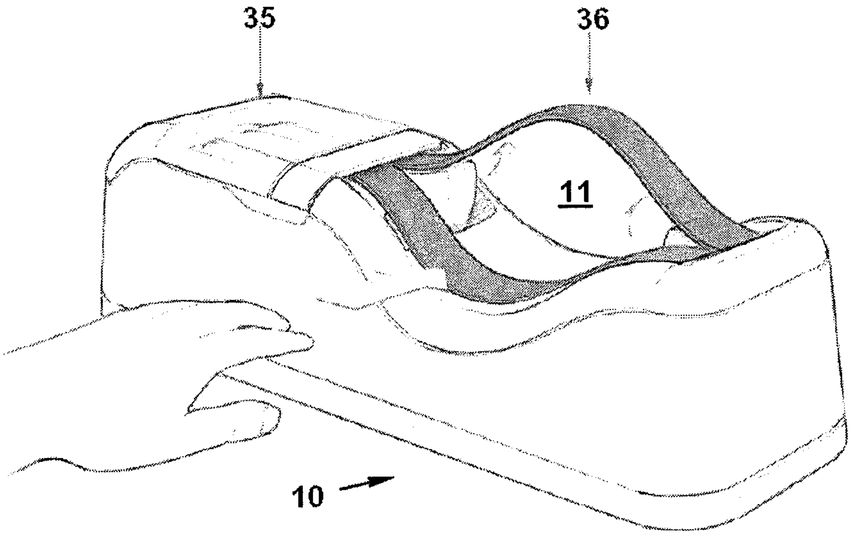
Figure 8A:
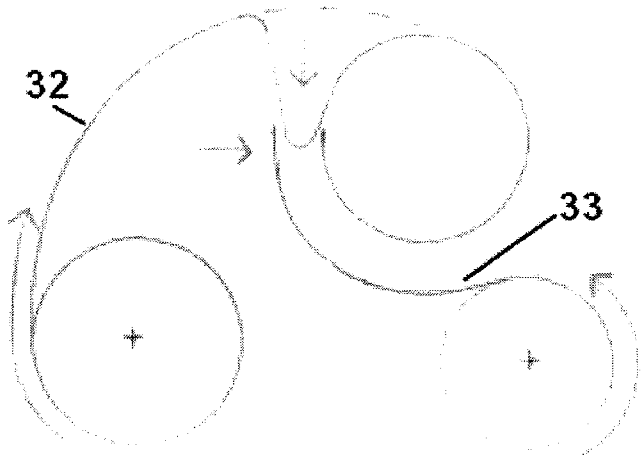
FIGS. 8*a*, 8*b*, 8*c*, 8*d*, 8*e*, and 8*f* show a schematic of the flow of the wristband material through the corresponding machines of FIGS. 7*a* to 7*f*.
Figure 8B:
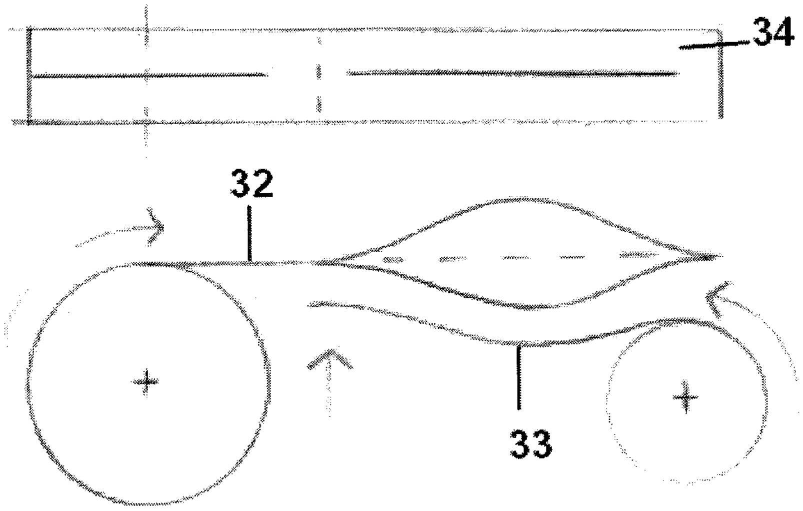

In FIG. 7*b*, another approach is illustrated, with an apparatus 10 supplying wide strip material 35 along the path 32 shown in FIG. 8*b*. The centre of the wide strip is sliced along a significant section 34, as shown in FIG. 8*b*. The apparatus 10 orientates the two sliced portions to create a void 36 between the two portions, and a person's arm is placed through this central void. The wristband is tensioned, and the seal is applied, following the path 33 shown in FIG. 8*b*. The seal may be applied in the "cufflink" manner, to provide a band as shown in FIG. 6*b*.

Figure 7C:
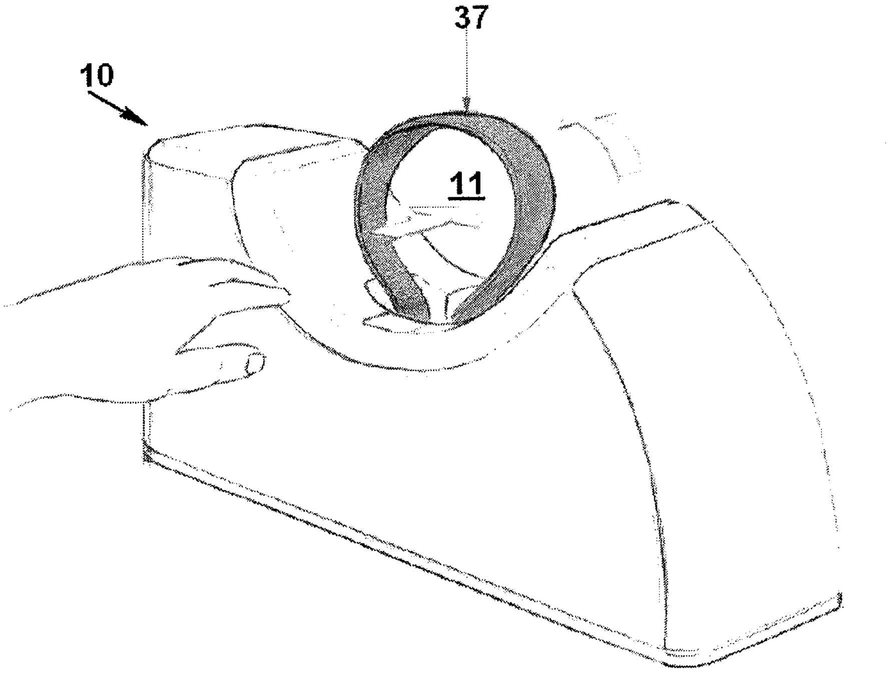
Figure 8C:
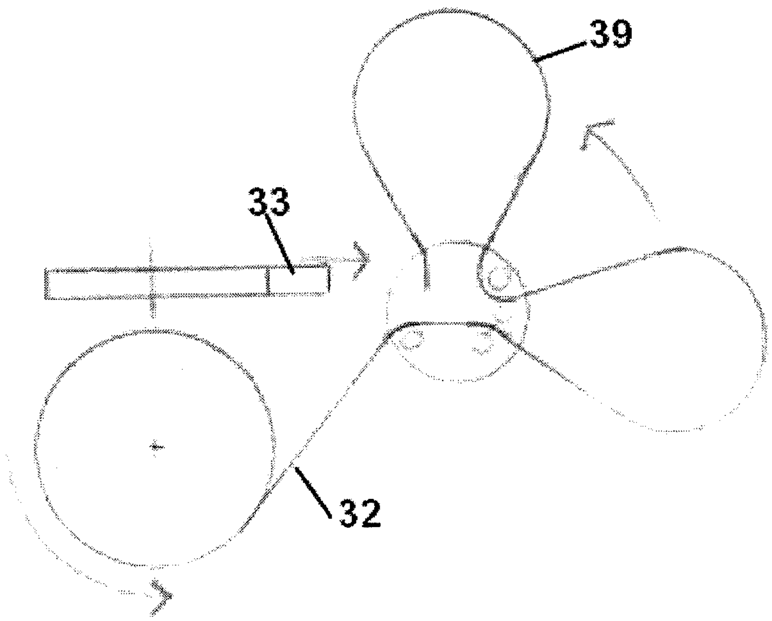

In FIG. 7*c*, another variation is shown, whereby a loop 37 of wristband material is created, through which an arm of a person is inserted. The path of the band material 32 is indicated in FIG. 8*c*, and this arrangement allows for there to be a stand-by loop, that is rotated to become the active loop 39 at the same time. A seal 33 is applied and the material is cut at the appropriate position, to provide a wristband as shown in FIG. 6*c*.

Figure 7D:
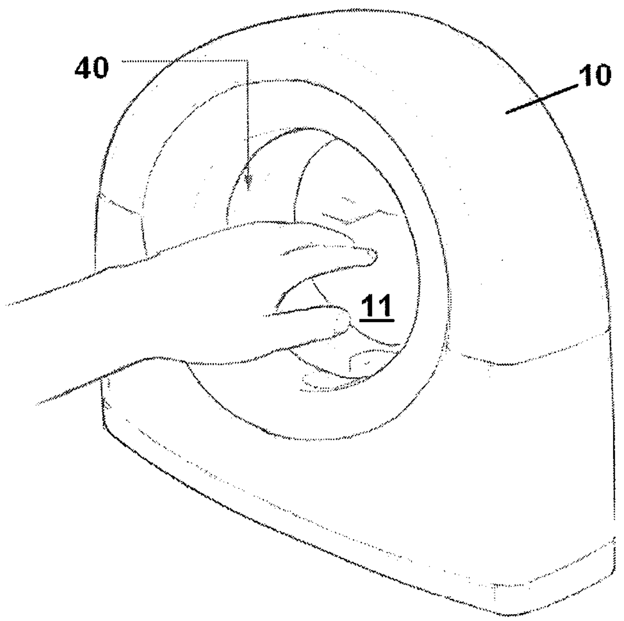
Figure 8D:
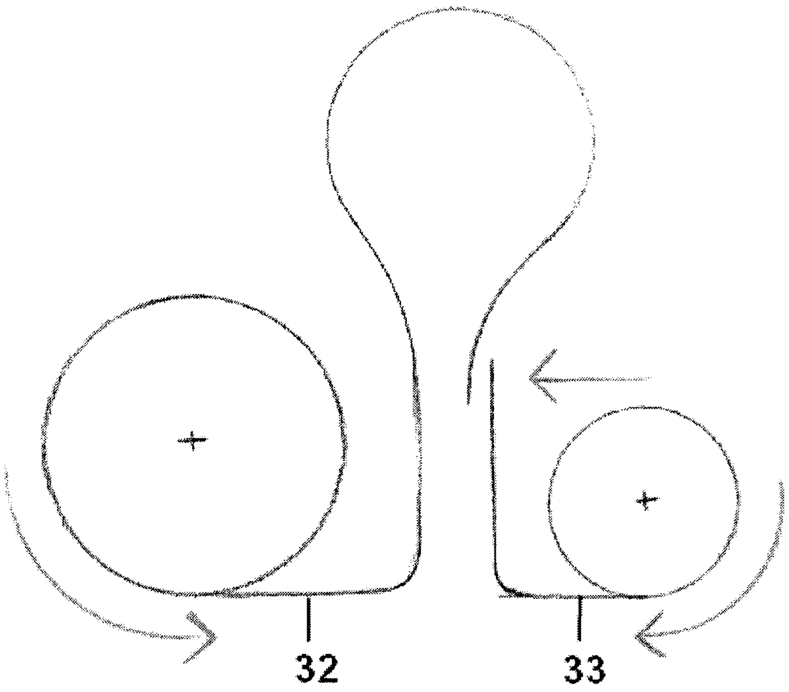

An enclosed design for the wristband application apparatus 10 is provided in FIG. 7*d*, where a person places their wrist inside an aperture 11. The wristband material 40 follows the general path 32 shown in FIG. 8*d*, and is hidden from view, until it is tensioned, cut to length and fastened together using a seal 33, which is applied as indicated in FIG. 8*d*.

Figure 7E:
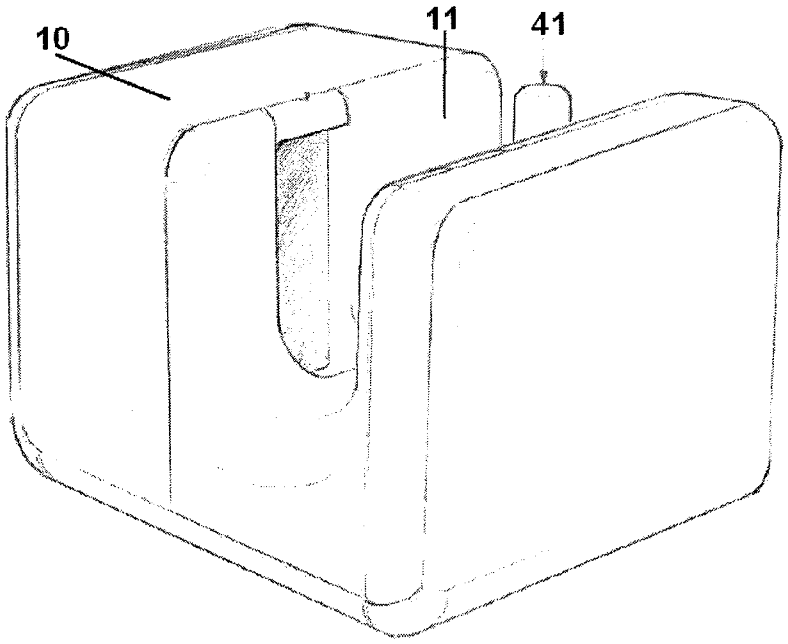
Figure 8E:
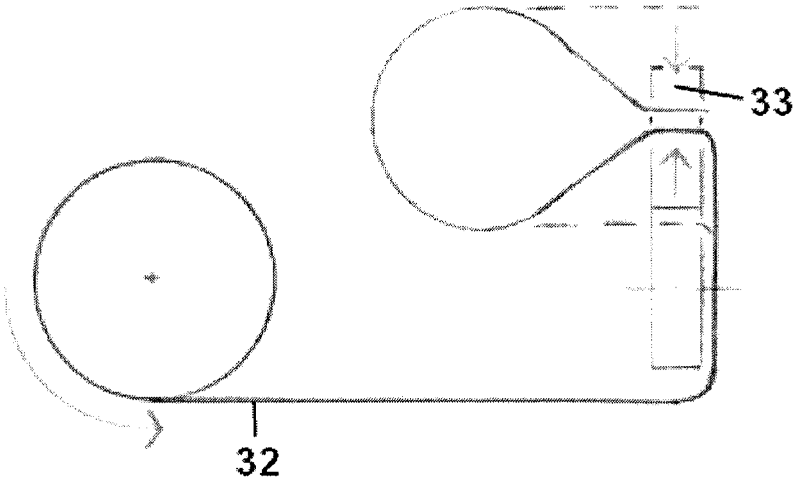

The apparatus 10 in FIG. 7*e*, has an open aperture 11, into which the arm of a person is placed. A hand grip 41 is also provided, so that the person can position their wrist generally at the right spot within the open aperture. The band material follows the path 32 as shown in FIG. 8*e*, and the seal 33 is applied, resulting wristband is as shown in FIG. 6*e*.

Figure 7F:
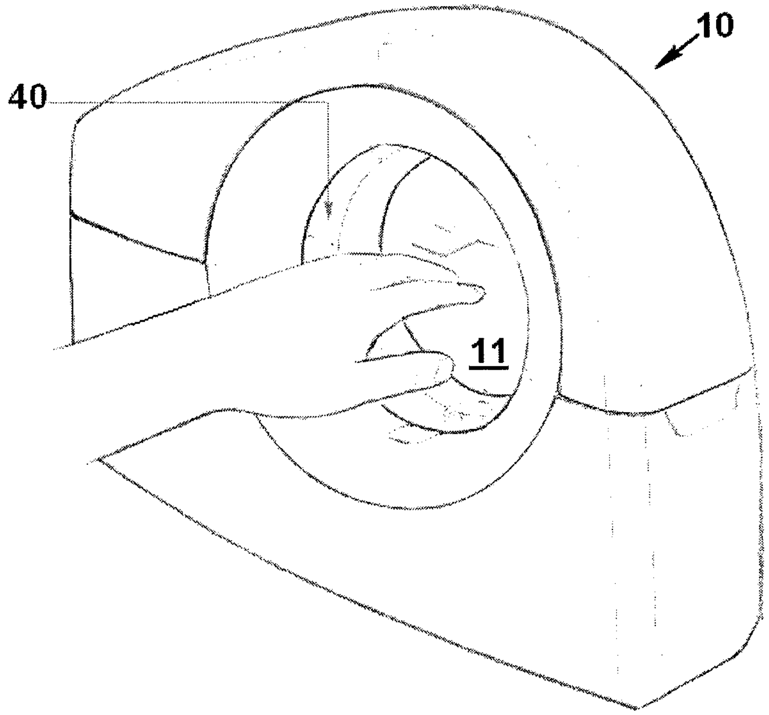
Figure 8F:
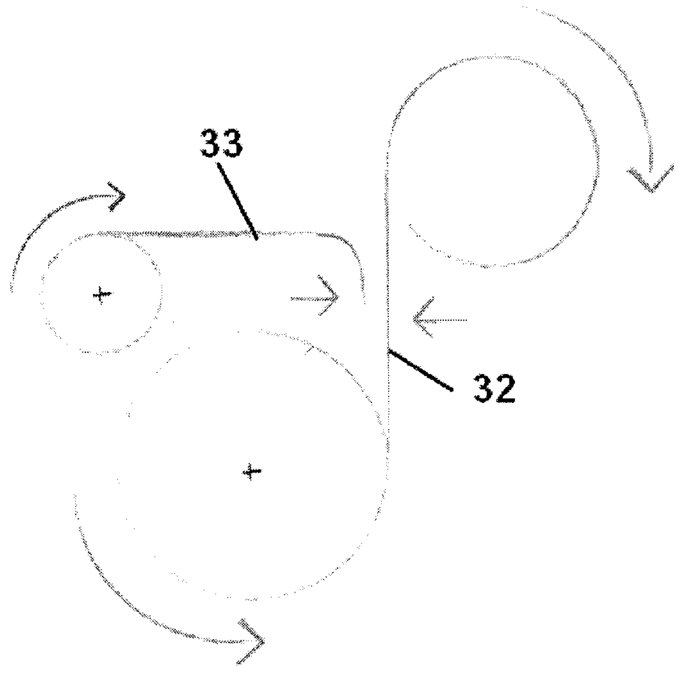

Another enclosed design for the wristband application apparatus 10 is provided in FIG. 7*f*, where a person places their wrist within an aperture 11. The wristband material 40 follows the general path 32 shown in FIG. 8*f*, and is hidden from view, until it is tensioned cut to length and fastened together using a seal 33, which is applied as indicated in FIG. 8*f*. The wristband can be sealed together as shown in FIG. 6*f*.

Figure 5A:
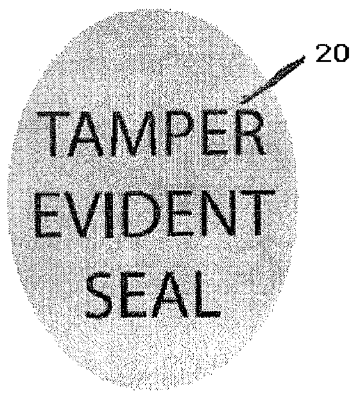
FIGS. 5*a* and 5*b* shows a tamper evident adhesive seal that can be utilised in accordance with the present invention.
Figure 5B:
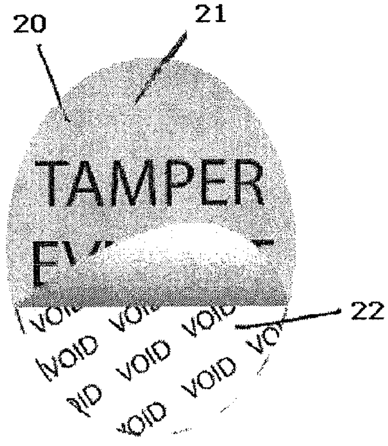

One example of the seal that may be utilised in the invention is shown in FIG. 5. A seal 20 is shown in FIG. 5*a*, and this may have information printed on its top surface. In one embodiment, the seal is in two layers, a top, outer layer 21 that is of a strong material, and has high integrity. There may also be an inner layer 22, which is a thin adhesive layer that has low integrity. This inner, adhesive layer 22 fixes the top layer of the seal to the two portions of the band surface.

As a preferred option, the inner layer may have information displayed on its outer surface that becomes visible when the other layer is removed. Ideally, the adhesion of the inner side of the inner layer that attaches to the band surface is stronger than the adhesion of the other side that attaches to the outer layer of the seal. This will cause the inner layer adhering to the band material, when the other layer of the seal is pealed away. If information is printed on the surface of the inner layer, it will then become visible. This information may comprise the word "void" or similar text that will clearly indicate that the seal has been removed or tampered with.

It is also preferred that the apparatus 10 is installed in a kiosk or other self service device, which permits the fast and efficient issuance of wristbands to a person, without the need for constant supervision by other personnel. The device may be positioned at a location that is convenient for patrons to insert their arm into the device. The device may be provided outside a venue, or else, may be in an entry corridor, permitting a queue of people to quickly be catered for. The kiosk may also have means to permit the person to pay for access to the venue, which operates the wristband application machine. For example, a person may insert their credit card into a slot, which starts the process, and then they are prompted, once the credit limit is checked and the card validated, to insert their wrist into the aperture for the wristband to be applied. Additionally, the kiosk may have a money validator with a cash box to accept cash transactions. It may be possible to remotely change the pricing levels on wristbands dispensed through a kiosk wristband applicator during the working day, which has the advantage of enabling end of day special discounts to be offered in real time. Likewise, it should also be possible to remotely cancel or suspend a transaction, or entitlement, for a rogue patron who has been evicted or suspected of fraud.

In another variation, the kiosk accepts online payments, such as credit card sales, and can carry out the transaction securely and reliably. This has the advantage of decreasing the order response time and enabling automated invoice issuing.

In another embodiment, the apparatus 10 may also have means to identify the person, and to confirm their right to enter a venue, before issuing and applying the wristband to an extremity of the person. For example, people may have previously purchased entry into the venue over the Internet. That process may have provided the patron with a password, or serial number, which they can then key into a touchpad on the kiosk, which will then permit the person to have a wristband applied. Patrons may select their requirements by pre-punching their password, or serial number, and credit card details, and inserting the credit card into the applicator. There may be a high speed image scanner to read the encoded barcode or RFID inlay data of the wristband and to check that this corresponds to the pre-purchased entry.

The apparatus 10 may also include a touch screen for ease of use, which can be either a flat panel display (FPD) or a cathode ray tube (CRT) display. The touch screen allows the customer to readily input data, such as credit card details and the like, into the apparatus 10 to facilitate the issue of the wristbands. An audio sound system may optionally be activated from the central system of the apparatus 10, with audio feedback acknowledging the touch screen selection to reinforce user confidence.

The apparatus 10 may also include an additional printer for the printing of receipts. Preferably, the printer chosen for this purpose is a high speed dpi thermal printer, with a preferred resolution of 200 dpi. The apparatus 10 may also contain a biometric fingerprint sensor to capture the fingerprint images of the customer. These captured fingerprints can then be used to match the uniqueness of each print read by the sensor with the one stored in its module or local system database in order to verify the identity of the patron. Further, the apparatus 10 may contain a proximity sensor to detect the presence of nearby objects without any physical contact from a user. This increases the efficiency of the apparatus 10 by triggering the apparatus to commence a warm up or application cycle.

Another advantage of the apparatus 10 is that it requires a person to position themselves in a specific area, for their wrist to be inserted into the apparatus in order to have the wristband correctly applied. This allows for other functions requiring the precise positioning of a person to occur. For example, the person's image may be captured at this location, as the person's face will be reasonably well located in front of a camera, web camera or video camera. A photo may be retained for security purposes, or else printed on the wristband, as a further feature. Any images captured on film or CCD and stored in a database can be used for the purpose of age verification at places such as night clubs in order to ensure the responsible service of alcohol or gaming and to minimise the potential for inadvertently serving alcohol to minors or similarly, allowing underage patrons to gamble. A TV tuner/video capture system may also be used to record any transactions made using the apparatus 10 of the present invention. It may also be possible to view live status reports, including real time sales, on wristband sales from the apparatus 10 using any Internet connected PC, including those that are remote from the location of the apparatus.

Other functions that may be included in the apparatus 10 of the present invention include, measuring the person's weight, if they are required to stand on a scale. The person's body height may also be easily measured or estimated as a consequence of this or an alternative height indicating sensor. Another function, may be to display a message on a screen positioned on the kiosk wall directly in front of the person, such as the requirements and restrictions on entry into the venue, and possibly it may also require the person to indicate their acceptance of these requirements.

It is preferred that the identity bracelet is able to go around a human wrist, but it may be utilised for identifying any animal, and as such, it is able to be fitted around the extremity of such an animal. It may also be fitted around any extremity, such as an arm, a leg, a neck, or even an ear. For example, it may otherwise be fitted around the hoof of a horse, or the ankle of a person, instead of around person's wrist.

An alternative set up of the present invention proposes that the wristband applicator apparatus 10 is mobile and specifically configured for ease of transport. In this variation, the keyboard and LCD touch screen fold into the main terminal.

All variations of the applicator apparatus 10 described above, include a system whereby faults are diagnosed and service requests can be reported to designated service agents. This ensures that all services are maintained in a timely and acceptable fashion. A warning notice is sent via SMS to event staff when the replenishment of consumables is required, such as replacement strips, seals, bands, receipts and the like, thereby minimising potential down time of the apparatus.

Industrial Applicability

The invention can be utilised in connection with security or other wrist bands, and to a system of applying such wristbands to people.

The word "comprising", or similar words, is generally intended to be interpreted in an inclusive sense, rather than exclusively, unless specifically indicted otherwise, and would normally allow other examples or features to be included.

It will be apparent that obvious variations or modifications may be made in accordance with the spirit of the invention that are intended to be part of the invention, and any such obvious variations or modification are therefore within the scope of the invention.

The invention claimed is:

1. An apparatus for dispensing and applying an identification bracelet that is attachable around an extremity of an animal, including a person, the apparatus being provided with a supply of identity bands that are adapted to become a bracelet by having a first portion of the band affixed to a second portion of the band to form a continuous loop around the extremity, characterised in that the extremity is positioned within a receptacle in the apparatus to permit the identification band to be wrapped closely around the extremity by band fixing means of the apparatus, and fixed to itself to form a bracelet, so as to prevent its removal from the extremity without damaging the integrity of said bracelet and wherein the band has identification information applied in the form of an RFID tag or inlay, and the identification includes RFID data.

2. The apparatus of claim 1, wherein the band is provided in the form of a continuous strip feedstock, which is cut to a suitable length by a cutting means of the apparatus.

3. The apparatus of claim 1, further comprising:

tensioning means to tauten the band close to the surface of the extremity, wherein the tensioning means is auto-tensioning to cater for a full range of the circumference size of the extremity; or self-adaptive length dispensing means to cater for a full range of the circumference size of the extremity.

4. An apparatus for dispensing and applying an identification bracelet that is attachable around an extremity, of an animal. including a person, the apparatus being provided with a supply of identity bands that are adapted to become a bracelet by having a first portion of the band affixed to a second portion of the band to form a continuous loop around the extremity, characterised in that the extremity is positioned within a receptacle in the apparatus to permit the identification band to be wrapped closely around the extremity by band fixing means of the apparatus, and fixed to itself to form a bracelet, so as to prevent its removal from the extremity without damaging the integrity of said bracelet, and wherein the band has identification information including at least one of printed characters, barcode, OCR, or photo images applied to its outer surface by an information application device of the apparatus.

5. An apparatus for dispensing and applying an identification bracelet that is attachable around an extremity of an animal, including a person, the apparatus being provided with a supply of identity bands that are adapted to become a bracelet by having a first portion of the band affixed to a second portion of the band to form a continuous loop around the extremity, characterised in that the extremity is positioned within a receptacle in the apparatus to permit the identification band to be wrapped closely around the extremity by band fixing means of the apparatus, and fixed to itself to form a bracelet, so as to prevent its removal from the extremity without damaging the integrity of said bracelet and further including seal application means for fixing the band to itself by a separate adhesive seal that is applied to the surface of the band, to overlap the first and second portions of the band.

6. An apparatus for dispensing and applying an identification bracelet that is attachable around an extremity of an animal, including a person, the apparatus being provided with a supply of identity bands that are adapted to become a bracelet by having a first portion of the band affixed to a second portion of the band to form a continuous loop around the extremity, characterised in that the extremity is positioned within a receptacle in the apparatus to permit the identification band to be wrapped closely around the extremity by band fixing means of the apparatus, and fixed to itself to form a bracelet, so as to prevent its removal from the extremity without damaging the integrity of said bracelet, and further comprising control means to govern the operation of the apparatus; and information reading and analysis means adapted to read any form of identification on the band, confirm that the identification is correct, and provide a warning if the identification cannot be read.

7. An apparatus for dispensing and applying an identification bracelet that is attachable around an extremity of an animal, including a person, the apparatus being provided with a supply of identity bands that are adapted to become a bracelet by having a first portion of the band affixed to a second portion of the band to form a continuous loop around the extremity, characterised in that the extremity is positioned within a receptacle in the apparatus to permit the identification band to be wrapped closely around the extremity by band fixing means of the apparatus, and fixed to itself to form a bracelet, so as to prevent its removal from the extremity without damaging the integrity of said bracelet, and further comprising positioning means adapted to ensure the extremity is optimally positioned within the apparatus, so that the band is applied around the correct area of the extremity, wherein the positioning means is a hand grip, so arranged that by holding the grip, the extremity of the person is properly positioned within the apparatus to receive the band.

8. The apparatus of claim 7, which is installed in a standalone kiosk, wherein the kiosk further includes means to accept payment from a person, prior to issuance and application of the bracelet and means to identify the person, and to confirm their right to enter a venue, before issuing and applying the bracelet to an extremity of the person.

9. An identity bracelet that is attachable around an extremity of an animal, including a person, said bracelet being attachable by means of an apparatus, whereby the apparatus is provided with a supply of identity bands that are adapted to become a bracelet by having a first portion of the band affixed to a second portion of the band to form a continuous loop around the extremity;

the extremity is positioned within a receptacle in the apparatus, to permit the identification band to be wrapped closely around the extremity by band fixing means of the apparatus, and fixed to itself to form a bracelet, so as to prevent its removal from the extremity without damaging the integrity of the bracelet;

characterised in that the bracelet is affixed to itself by means of a separate adhesive seal, which is applied to the surface of the band, to overlap the first and second portions of the band, the seal being applied by way of seal application means of the apparatus.

10. The identity bracelet of claim 9, wherein the seal comprises a first inner layer, which is a thin adhesive layer that has low integrity having an inner side and an outer side, and a second outer layer, which is of a material that is sufficiently strong to retain the bracelet together, whereby the inner layer adheres the outer layer to the band.

11. The identity bracelet of claim 10, wherein the inner layer of the seal has information displayed on its outer surface that becomes visible when the outer layer is removed; and wherein said information is text, such as the word “void”, or a similar word or words.

12. The identity bracelet of, claim 9, further comprising an RFID functional inlay component; wherein the RFID functional inlay component comprises a silicon CMOS integrated circuit (IC) combined with an antenna; wherein the RFID functional inlay component includes electronic circuitry that is created entirely by means of a semiconductor printing process; wherein the CMOS integrated circuit is implemented using nanoparticle formulated “silicon ink”materials to create complementary P and N channel thin-film-transistor (TFT) semiconductor devices; and wherein the antenna is printed with conductive metal particle ink by high speed ink-jet deposition directly onto a substrate carrier comprising a polymer plastic material band.

13. The identity bracelet of claim 9 substantially of a laminated polymer plastic material band, which is attachable around an extremity of an animal, including a person, by a bracelet applicator device, wherein the RFID functional inlay component and the antenna are sandwich laminated into the polymer plastic material band or hermetically sealed into the polymer plastic material band either by the apparatus during the continuous wristband lamination process or being integrally formed with the bracelet during the continuous lamination process and wherein the RFID functional inlay component has a polymer backing layer.

* * * * *